United States Patent [19]
Taki et al.

[11] Patent Number: 5,891,058
[45] Date of Patent: Apr. 6, 1999

[54] COILED EMBOLIZING MATERIAL

[75] Inventors: Waro Taki, Osaka; Atsushi Ogawa, Kanagawa, both of Japan

[73] Assignee: Kaneka Medix Corporation, Osaka, Japan

[21] Appl. No.: 907,236

[22] Filed: Aug. 6, 1997

[30] Foreign Application Priority Data

Aug. 15, 1996 [JP] Japan .................................. 8-215553

[51] Int. Cl.⁶ ....................................................... A61B 5/00
[52] U.S. Cl. ............................................ 600/585; 606/191
[58] Field of Search .................................... 600/433–436, 600/585; 606/191, 198, 200

[56] References Cited

U.S. PATENT DOCUMENTS

| | | | |
|---|---|---|---|
| 4,676,249 | 6/1987 | Arenos et al. ........................... | 600/585 |
| 4,739,768 | 4/1988 | Engelson ................................. | 128/658 |
| 4,884,579 | 12/1989 | Engelson ................................. | 128/772 |
| 5,649,949 | 7/1997 | Wallace et al. . | |

FOREIGN PATENT DOCUMENTS

| | | |
|---|---|---|
| 547530 | 6/1993 | European Pat. Off. . |
| 719522 | 7/1996 | European Pat. Off. . |
| 6-246004 | 9/1994 | Japan . |
| 7-265431 | 10/1995 | Japan . |
| 7-284534 | 10/1995 | Japan . |
| WO 91/13592 | 9/1991 | WIPO . |
| WO 94/06503 | 3/1994 | WIPO . |
| WO 95/11055 | 4/1995 | WIPO . |
| WO 95/12367 | 5/1995 | WIPO . |

*Primary Examiner*—Max Hindenburg
*Attorney, Agent, or Firm*—Frishauf, Holtz, Goodman, Langer & Chick, P.C.

[57] ABSTRACT

A coiled embolizing material which can surely embolize an application site or dilatation without extending either end portion thereof out of the dilatation. The distal end portion and/or the proximal end portion of the coiled embolizing material are curved inward in a radial direction of a coil thereof. A push-out means for the embolizing material is detachably connected to the coiled embolizing material.

20 Claims, 6 Drawing Sheets

COILED EMBOLIZING MATERIAL

BACKGROUND OF THE INVENTION

1) Field of the Invention

The present invention relates to a coiled embolizing material to be deposited at an intended site in a vasculature of, for example, a human body.

2) Description of the Background Art

As a method for treating an aneurysm or the like, which causes little invasion, attention has been recently attracted to vascular embolization in which an embolizing material is deposited within a dilatation. Reference may be made to, for example, U.S. Pat. Nos. 4,884,579 and 4,739,768. In this vascular embolization, the embolizing material deposited within the aneurysm serves as a physical obstacle to a blood stream and can facilitate the formation of thrombus to reduce the risk of aneurysmal rupture.

As the embolizing material to be deposited at an intended site in the vasculature, coiled embolizing materials have been known.

Such a coiled embolizing material is introduced into an aneurysm through a suitable catheter by means of a wire-made push-out device or a guide detachably connected to an end thereof. Reference may be made to, for example, Japanese Patent Application Laid-Open (KOHYO) Nos. 500322/1993, 501015/1996 and 502674/1995 (through PCT route)

More specifically, the coiled embolizing material, to which the push-out device has been connected, is inserted into the catheter, which has been inserted into the vital body in advance in such a manner that its distal opening is sited within the aneurysm, with the coiled embolizing material in the lead. As a result, the embolizing material is transferred through the catheter while being pushed by the push-out device, whereby it is pushed out of the distal opening of the catheter into the dilatation. At the time the whole length of the embolizing material has been pushed out of the distal opening, namely, its joint with the push-out device has reached the distal opening, the push-out device is detached from the embolizing material making good use of a mechanical means, electrolysis or the like, whereby only the embolizing material is deposited within the aneurysm.

FIG. 1 illustrates a conventional coiled body making up a coiled embolizing material.

This coiled body 1 is a helical double-coiled body having deformability. A semi-spherical tip 2 is formed at one end thereof.

Since the coiled body 1 has deformability, it shows a state that it is stretched in a substantially straight line along a catheter when it is pushed by a push-out device to move through the catheter, and returns to the original double-coiled body (the shape illustrated in FIG. 1) when it is pushed out of the catheter into an aneurysm, and the push-out device is detached from the coiled body.

By the way, in order to surely embolize the interior of an aneurysm, it is important to deposit the coiled embolizing material within the aneurysm so as to fit it to the inner wall of the aneurysm.

Therefore, the outer diameter of the coiled body making up the embolizing material (for example, the outer diameter of the double-coiled body illustrated in FIG. 1) must be generally made somewhat greater than the inner diameter (the inner diameter when an internal space of the aneurysm is regarded as a sphere) of the aneurysm in which the coiled body should be deposited.

When the outer diameter of the coiled body making up the embolizing material is greater than the inner diameter of the aneurysm, however, there is a problem that an end portion of the coiled body is extended out of the dilatation.

More specifically, as illustrated in FIG. 2A, in some cases, a distal end portion 5A of a coiled body 5, which has been pushed out of a distal opening of a catheter 3 into an aneurysm 4, may extend out of the opening of the aneurysm 4 into a parental blood vessel 6 outside the dilatation.

Besides, as illustrated in FIG. 2B, in some cases, a proximal end portion 5B of the coiled body 5 deposited within the aneurysm 4 after a push-out device (not illustrated) is detached, may extend out of the opening of the aneurysm 4 into the parental blood vessel 6 outside the dilatation.

Such a state as described above particularly tends to occur when an aneurysm to be embolized has a slender form. When the distal or proximal end portion of the coiled body extends out of the dilatation, a thrombus is formed on the end portion of the coiled body extended out of the dilatation, and so the parental blood vessel is occluded by the thrombus, or the thrombus transmigrates to a peripheral vessel, thereby occluding such a peripheral vessel.

SUMMARY OF THE INVENTION

The present invention has been completed under the foregoing circumstances. It is an object of the present invention to provide a coiled embolizing material, which can surely embolize an application site without extending either end portion thereof out into a vessel, for example, a parental blood vessel outside a dilatation, outside the application site.

The above object can be achieved by the present invention described below.

According to the present invention, there is thus provided a coiled embolizing material to be deposited at an intended site in a vasculature, wherein at least one end portion of the embolizing material is curved inward in a radial direction of a coil thereof.

The coiled embolizing material according to the present invention may comprise a double-coiled body, wherein at least one end portion of the double-coiled body is curved inward in a radial direction of a secondary coil thereof.

In the coiled embolizing material according to the present invention, a push-out device for the embolizing material may preferably be detachably connected to the embolizing material.

In the coiled embolizing material according to the present invention, the push-out device for the embolizing material may preferably be detachably connected to the embolizing material through a joint member. Particularly, the joint member may preferably be formed of poly(vinyl alcohol) or a vinyl alcohol copolymer.

Since one end portion and/or the other end portion of the coiled embolizing material according to the present invention is curved inward in the radial direction of the coil, the coiled embolizing material can be deposited at an application site in a state that it is fitted to the inner wall of the application site, and moreover the end portion of the coiled embolizing material can be prevented from extending out into a vessel outside the application site.

In insertion of the coiled embolizing material into the application site or dilatation, the coiled embolizing material having the distal end portion curved inward moves along the inner wall of the application site in a state that the distal end thereof points to the interior of the dilatation. Therefore, the distal end portion of the embolizing material pushed out of the distal opening of, for example, a catheter into the aneurysm does not damage the inner wall surface of the aneurysm, and is surely present in the aneurysm, thereby preventing it from extending out of the dilatation into a parental blood vessel.

When the push-out device is detached from the coiled embolizing material introduced into the application site or dilatation, the coiled embolizing material having the proximal end portion curved inward returns to a state that the proximal end thereof points to the interior of the dilatation. Therefore, the proximal end portion of the embolizing material deposited into the aneurysm is surely present in the aneurysm, thereby preventing it from extending out of the dilatation into a parental blood vessel.

The above and other objects, features and advantages of the present invention will become apparent from the following description and the appended claims, taken in conjunction with the accompanying drawings.

DETAILED DESCRIPTION OF THE INVENTION AND PREFERRED EMBODIMENTS

The present invention will hereinafter be described in detail according to the embodiments of the present invention with reference to the drawings.

First embodiment

Figure 1:
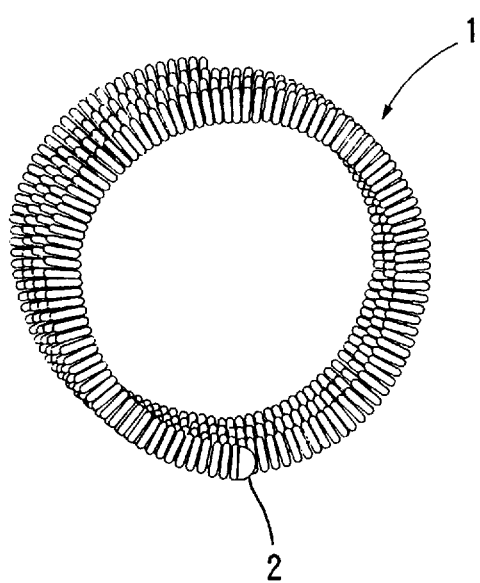
FIG. 1 schematically illustrates the conventional coiled body making up a coiled embolizing material.
Figure 2A:
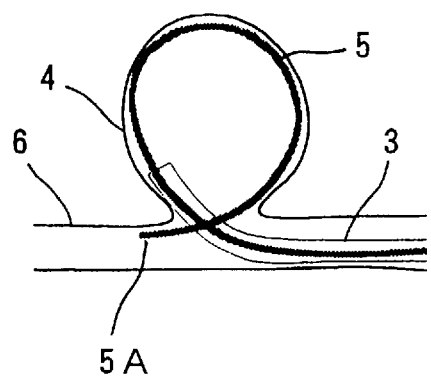
FIGS. 2A and 2B schematically illustrate a state that an end portion of the coiled body of the conventional embolizing material, which has been introduced into an aneurysm, extends out into a parental blood vessel outside the dilatation.
Figure 2B:
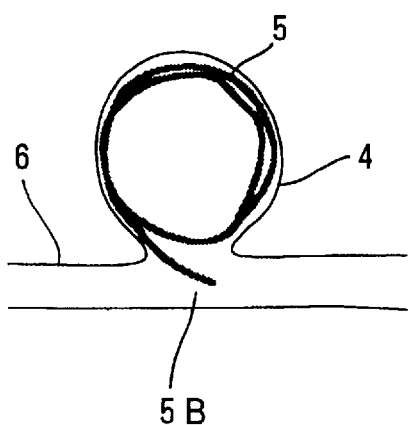
Figure 3:
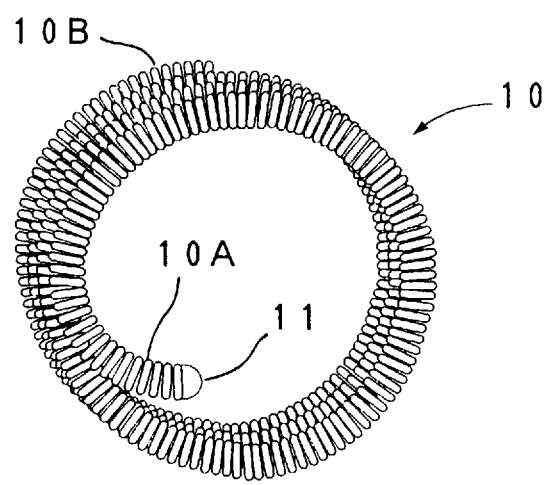
FIG. 3 illustrates an example of a coiled body making up a coiled embolizing material according to the present invention.

FIG. 3 illustrates an example of a coiled body making up a coiled embolizing material according to the present invention. The coiled body 10 is composed of a helical double-coiled body having deformability and is so constructed that a distal end portion 10A thereof is curved inward in a radial direction of a secondary coil thereof. Reference numeral 11 denotes a tip mounted at a distal end of the coiled body 10. The tip 11 is formed in a semi-spherical shape having a smooth surface by, for example, melting a wire for the coiled body from the viewpoint of preventing an application site from being damaged.

The coiled body 10 is preferably formed from a wire capable of being observed by X-ray fluoroscopy, such as platinum, gold, tungsten or an alloy thereof. A diameter of the wire for forming the coiled body 10 is about 0.02–0.12 mm.

The coiled body 10 is a helical double-coiled body obtained by winding the above-described wire to form a primary coil and further winding the primary coil to form a secondary coil. A diameter of the primary coil is generally 0.1–1.0 mm, preferably 0.2–0.5 mm, while a diameter of the secondary coil is suitably selected according to the inner diameter of an application site, for example, an aneurysm, but is generally 2–40 mm, preferably 2–20 mm.

The coiled body 10 has a feature that the distal end portion 10A thereof is curved inward in the radial direction of the secondary coil. The length of the curved portion or the distal end portion 10A is generally at least 0.25 L, preferably 0.25 L–0.5 L wherein L denotes a perimeter of unit coil of the secondary coil. If the length of the curved portion is too short, it is impossible to sufficiently prevent the distal end portion from extending out of the dilatation. On the other hand, if the length of the curved portion is too long, it is impossible to maintain a state that the coiled body has been fitted to the inner wall of the application site. The curved portion or the distal end portion 10A of the coiled body 10 may have either the same curvature or an increasing curvature, for example, clothoid, toward the distal end. When the curved portion has the same curvature, the curvature of the curved portion is preferably greater than that of the inner wall of the application site. The distal end portion 10A may be wound at least one turn along a circle of a diameter smaller than that of the secondary coil.

Figure 5A:
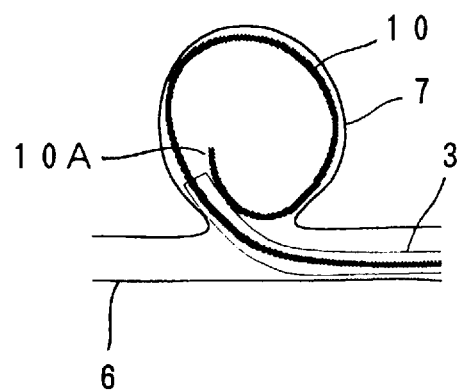
FIGS. 5A and 5B schematically illustrate a state that an end portion or end portions of each coiled body of the embolizing materials according to the present invention, wherein each have been introduced into an aneurysm, are present in the application site.

A push-out device is connected to a proximal end 10B of the coiled body 10, and the coiled body 10 is introduced into the application site through a suitable catheter 3, whereby the distal end portion 10A of the embolizing material 10 pushed out of the distal opening of the catheter 3 into the application site 7 neither sticks in the inner wall surface nor damages it and is surely present within the application site 7, as illustrated in FIG. 5A, and so it is prevented from extending out into a parental blood vessel 6 outside the dilatation.

Second embodiment

Figure 4:
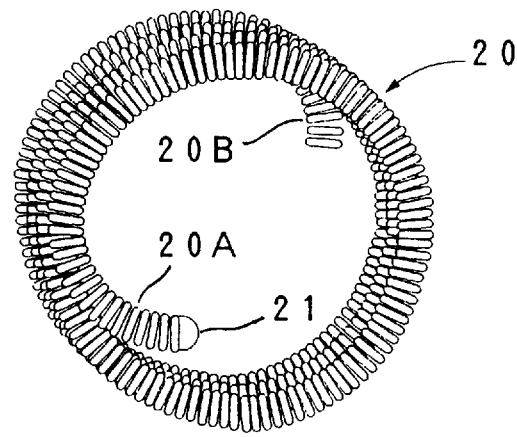
FIG. 4 illustrates another example of a coiled body making up a coiled embolizing material according to the present invention.

FIG. 4 illustrates another example of a coiled body making up a coiled embolizing material according to the present invention. The coiled body 20 is composed of a helical double-coiled body having deformability and is so constructed that both distal end portion 20A and proximal end portion 20B thereof are curved inward in a radial direction of a secondary coil thereof. Reference numeral 21 denotes a semi-spherical tip mounted or formed at a distal end of the coiled body 20.

The coiled body 20 has a feature that both distal end portion 20A and proximal end portion 20B thereof are curved inward in the radial direction of a secondary coil thereof. Other constructions thereof are the same as those described in the coiled body 10. Curving conditions such as length and shape for the proximal end portion 20B may also be the same as those for the distal end portions 20A.

Figure 5B:
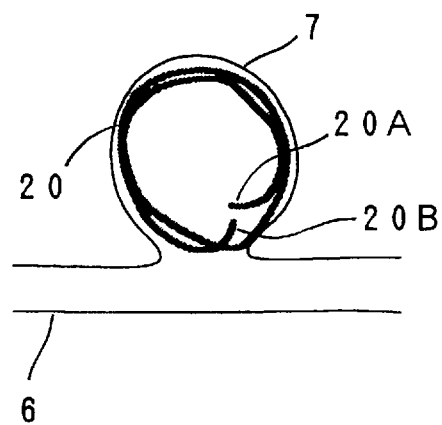

A push-out device is connected to a proximal end of the coiled body 20, and the coiled body 20 is introduced into the application site through a suitable catheter, whereby both distal end portion 20A and proximal end portion 20B of the embolizing material 20 deposited within the application site 7 are surely present within the application site 7, as illustrated in FIG. 5B, and so they are prevented from extending out into a parental blood vessel 6 outside the dilatation.

Third embodiment

Figure 6:
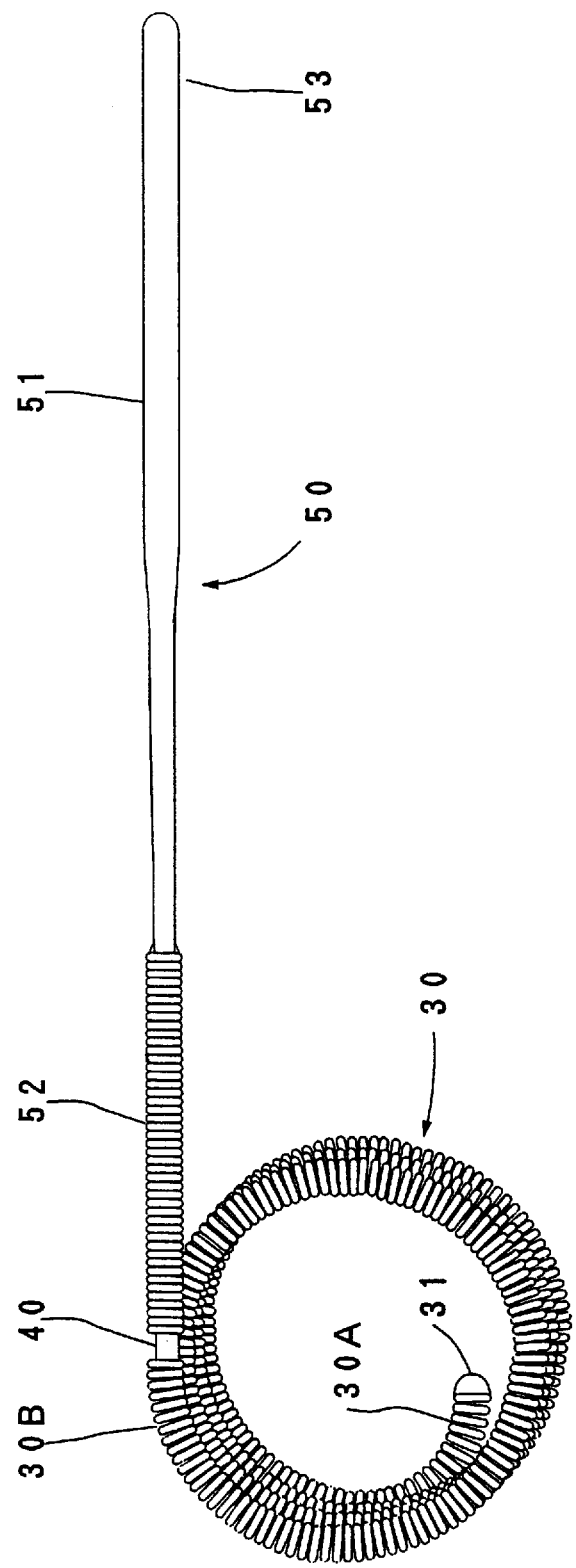
FIG. 6 illustrates a further example of a coiled body making up a coiled embolizing material according to the present invention.

FIG. 6 illustrates a further example of a coiled body making up a coiled embolizing material according to the present invention. A push-out device 50 for the embolizing material is connected to a proximal end of the coiled body 30 through a rod-like joint member 40. Reference numeral 31 denotes a semi-spherical tip mounted or formed at a distal end of the coiled body 30. The coiled body 30 has the same construction as the coiled body 20 according to the second embodiment, and so the proximal end portion 30B thereof is recovered so as to curve inward in a radial direction of a secondary coil thereof when the push-out means 50 is detached.

The push-out device 50 comprises a guide or coil pusher for introducing the coiled body 30 making up the embolizing material into an application site. The push-out device 50 includes a wire part 51 obtained by forming a coating layer of resin on a peripheral surface of a core wire and a distal X-ray impervious part 52 contiguous to the wire part. The push-out device 50 has an outer diameter of, for example, 0.1 to 2.0 mm and a length of, for example, 0.1–2.0 m. As the core wire making up the push-out device 50, there may be used a wire formed of a conductive material such as a stainless steel.

The coating layer of resin in the wire part 51 of the push-out device 50 can be formed by coating the peripheral surface of the core wire with, for example, a fluorocarbon resin or hydrophilic resin. The coating layer of resin formed of the fluorocarbon resin or hydrophilic resin is preferred in that the coefficient of friction of the surface can be made low. At the proximal end of the wire part 51, the core wire is exposed to form a terminal part 53 through which electric power can be supplied via suitable conductive members such as an electrical connector, plug and/or clip. About 1 to 3 cm suffice the length of this terminal part 53.

The distal X-ray impervious part 52 of the push-out device 50 is constructed by further closely winding a winding wire in the form of a coil on the peripheral surface of the core wire. As the winding wire making up the distal X-ray impervious part 52, there may be used a wire formed of a metal such as platinum, silver or tungsten.

The distal X-ray impervious part 52 of the push-out device 50 is connected and fixed to the proximal end of the coiled body 30 through the joint member 40. No particular limitation is imposed on the device for fixing the proximal end of the coiled body 30 to the joint member 40, and the means for fixing the distal X-ray impervious part 52 of the push-out device to the joint member 40. For example, bonding with an adhesive, welding, connection by physical force or the like may be used.

A material for the joint member 40 which is interposed between the coiled body 30 and the push-out device 50 may be any material so far as it does not adversely affect the vital body and can be melted and severed by heating. More specifically, poly(vinyl alcohol) or a vinyl alcohol copolymer, which is melted by heating, is preferred. However, the material for the joint member 40 is not limited to these polymers. For example, a material, which is deformed by heating, such as a shape-memory alloy or resin, may be used.

The coiled body 30 to which the push-out device 50 has been connected through the joint member 40 is introduced into an application site within the vital body via a suitable catheter.

Figure 7:
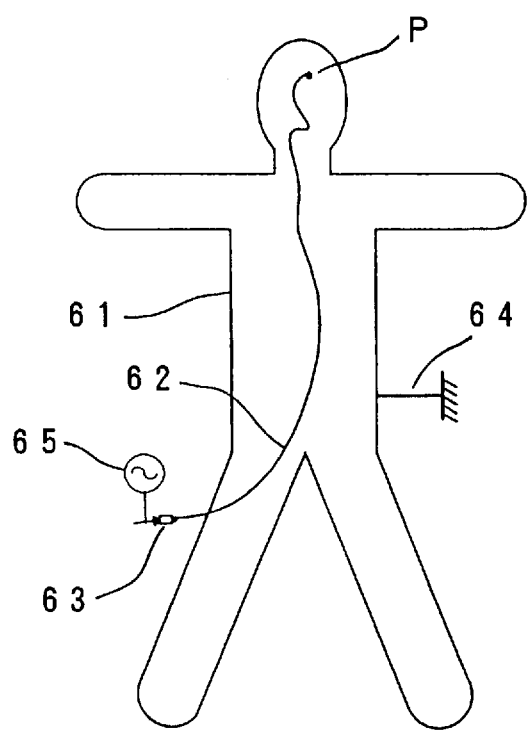
FIG. 7 schematically illustrates an application example of a coiled embolizing material according to the present invention.

More specifically, as illustrated in FIG. 7, the coiled body, for example, the coiled body 30 illustrated in FIG. 6, to which the push-out device has been connected, is inserted into a catheter 62, which has been inserted in advance in such a manner that the distal opening thereof reaches an application site P in the vital body 61, through a proximal operating part 63 of the catheter 62 with the coiled body in the lead. By this operation, the coiled body is transferred through the catheter 62 by being pushed by the push-out device in a state that the coil has been forcedly stretched in a substantially straight line along the catheter 62, whereby the coiled body is pushed out of the distal opening of the catheter 62 into the application site P. At the time the joint member reaches the distal opening of the catheter 62, an earth electrode 64 is attached to the skin surface of the vital body 61, and a high-frequency power source 65 is connected to the terminal part of the push-out device to supply, for example, a monopolar high-frequency current to the push-out device.

As a result, the joint member 40 interposing between the coiled body 30 and the push-out device 50 generates heat by the high-frequency current, and so the joint member 40 is melted and severed. Therefore, the coiled body 30 is separated from the push-out device 50, whereby an embolizing material composed of the coiled body 30 can be deposited within the application site. Since both distal end portion 30A and proximal end portion 30B of the coiled body 30 thus deposited are curved inward in the radial direction of the secondary coil thereof, they are prevented from extending out into a parental blood vessel outside a dilatation at the application site. As described above, when a material having sufficiently high stiffness and mechanical strength at the temperature of the human body, and a melting point of 100° C. or lower is selected as a material for the joint member 40, the joint member 40 can be heated and severed within a short period of time by supplying the high-frequency current thereto. More specifically, when the joint member 40 is formed of poly(vinyl alcohol) or a vinyl alcohol copolymer, the joint member 40 can be melted and severed by supplying a high-frequency current for an extremely short period within 3 seconds, for example. Therefore, burdens imposed not only on a surgeon, but also on a patient to be operated can be very lightened. In addition, a possibility that contingencies may occur on the vital body during the depositing operation can be lessened to a great extent.

The present invention will hereinafter be described more specifically by the following example. However, the present invention is not limited to and by this example.

EXAMPLE

Following the construction of FIG. 6, a proximal end of a joint member 40 formed of an uncrosslinked vinyl alcohol copolymer in the form of a columnar rod having a diameter of 0.2 mm and a length of 10 mm was bonded with an adhesive to a distal end of a push-out device 50 made of stainless steel having an outer diameter of 0.4 mm and an overall length of 1,800 mm and having a distal X-ray impervious part 52 of 30 mm in length. Further, a proximal end of a coiled body 30 was bonded to a distal end of the joint member 40 with an adhesive, thereby producing an embolizing material-introducing device having a coiled embolizing material or coiled body 30 according to the present invention. The coiled body 30 used was composed of a double-coiled body having a primary coil diameter of 0.4 mm and a secondary coil diameter of 14 mm, constructed by a platinum alloy wire having a diameter of 0.08 mm in such a manner that the distal end portion 30A of 10 mm and the proximal end portion 30B of 10 mm thereof were curved inward in a radial direction of the secondary coil thereof. The diameter of the curved portion was 10 mm in length.

The embolizing material-introducing device thus produced was inserted into a microcatheter 33, which had been inserted in advance so as to site the distal opening thereof at a human cerebral aneurysm, which was a substantially spherical dilatation having an inner diameter of about 13–14 mm, with the coiled body in the lead. At the time the whole length of the coiled body was pushed out of the microcatheter, an earth electrode was attached to the skin surface of the human body, and a high-frequency power source was connected to a terminal part of the push-out device to supply a high-frequency current of a frequency of 300 kHz and electric power of about 5–6 W to the push-out device. As a result, the joint member was instantaneously melted and severed to detach the coiled body from the push-out device, thereby completing the introduction of the coiled body which was the embolizing material according to the present invention. When the coiled body was observed by X-ray fluoroscopy, it was found that the coiled body returned to the original shape and was deposited within the aneurysm in a state that it was fitted to the inner wall of the aneurysm, and that both distal end and proximal end portions of the coiled body were present within the dilatation and did not extend out of the dilatation.

The coiled embolizing material according to the present invention is deposited in an application site so as to fit it to the inner wall thereof, thereby ensuring that the application site can be embolized. In addition, either end portion thereof is prevented from extending out into a vessel outside the application site, for example, a parental blood vessel outside the dilatation.

The site or dilatation which can be embolized by the coiled embolizing material according to the present invention is not limited to the spherical dilatation. According to the coiled embolizing material of the present invention, for example, such a slender dilatation that when the conventional helical coiled body is introduced therein, an end portion thereof extends out of the dilatation, can also be embolized without extending either end portion thereof out of the dilatation.

What is claimed is:

1. A coiled embolizing body comprising an elongated member made of an embolizing material for introduction at an intended site in a vasculature, said elongated member being in the form of a coil, said elongated member having at least one free end portion thereof which is curved inward in a radial direction of the coil.

2. The coiled embolizing body according to claim 1, wherein the elongated member is wound around an axis thereof to form a double-coiled body having a Primary coil and a secondary coil, at least one free end portion of the double-coiled body is curved inward in a radial direction of the secondary coil.

3. The coiled embolizing body according to claim 1, further comprising a push-out device for introducing the coiled embolizing body to the intended site, said push-out device being detachably connected to the coiled embolizing body.

4. The coiled embolizing body according to claim 3, wherein the push-out device is detachably connected to the coiled embolizing body through a joint member.

5. The coiled embolizing body according to claim 4, wherein the joint member is formed of poly(vinyl alcohol) or a vinyl alcohol copolymer.

6. The coiled embolizing body according to claim 2, further comprising a push-out device for introducing the coiled embolizing body to the intended site, said push-out device being detachably connected to the coiled embolizing body.

7. The coiled embolizing body according to claim 6, wherein the push-out device is detachably connected to the coiled embolizing body through a joint member.

8. The coiled embolizing body according to claim 7, wherein the joint member is formed of poly(vinyl alcohol) or a vinyl alcohol copolymer.

9. The coiled embolizing body according to claim 2, further comprising a semi-spherical shaped tip having a smooth surface which is disposed on said at least one free end portion.

10. The coiled embolizing body according to claim 9, wherein the coiled body is formed from a wire made of a metal selected from the group consisting of platinum, gold, tungsten and alloys thereof.

11. The coiled embolizing body according to claim 10, wherein the wire has a diameter of 0.02 to 0.12 mm.

12. The coil embolizing body according to claim 11, wherein the primary coil has a diameter of 0.1 to 1.0 mm and the secondary coil has a diameter of 2 to 40 mm.

13. The coil embolizing body according to claim 12, wherein the primary coil has a diameter of 0.2 to 0.5 mm and the secondary coil has a diameter of 2 to 20 mm.

14. The coil embolizing body according to claim 13, wherein the secondary coil has a perimeter of a length L and the portion which is curved inward in a radial direction of the secondary coil has a length of at least 0.25 L.

15. The coil embolizing body according to claim 14, wherein the portion which is curved inward in a radial direction of the secondary coil has a length of 0.25 L to 0.5 L.

16. The coil embolizing body according to claim 3, wherein both a distal end portion thereof and a proximal end portion thereof are curved inward in a radial direction of the secondary coil.

17. The coil embolizing body according to claim 16, wherein a semi-spherical tip is disposed at the distal end portion.

18. The coil embolizing body according to claim 4, wherein the push-out device is disposed at a proximal end of the coiled body and which further comprises a semi-spherical shaped tip having a smooth surface which is disposed at a distal end of the coiled embolizing body.

19. The coil embolizing body according to claim 18, wherein the joint member is made of poly(vinyl alcohol) or a vinyl alcohol copolymer and is meltable by heating.

20. A coiled embolizing body comprising an elongated member made of an embolizing material wound around an axis of the elongated member to form a primary coil, said primary coil being wound into a secondary coil having a diameter greater than that of the primary coil, said secondary coil having a free end portion which is curved inward in a radial direction of the secondary coil, said inward curved free end portion having a curvature which is greater than that of the secondary coil.

\* \* \* \* \*